United States Patent
Su et al.

(10) Patent No.: US 9,908,844 B2
(45) Date of Patent: Mar. 6, 2018

(54) EPOXY RESIN OLIGOMER WITH SECOND ORDER NONLINEAR OPTICAL PROPERTIES, CHROMOPHORES, AND METHOD OF MANUFACTURING THE OLIGOMER-CONTAINING CROSSLINK LAYERED EPOXY/MMT COMPOSITE MATERIAL WITH SECOND ORDER NONLINEAR OPTICAL PROPERTIES

(71) Applicant: NATIONAL CHUNG SHAN INSTITUTE OF SCIENCE AND TECHNOLOGY, Taoyuan (TW)

(72) Inventors: Wen-Chiung Su, Taoyuan (TW); Ru-Jong Jeng, Taipei (TW); Chien-Hsin Wu, Taipei (TW); Yu-Wen Lai, Taipei (TW); Shih-Chieh Yeh, Taipei (TW)

(73) Assignee: NATIONAL CHUNG SHAN INSTITUTE OF SCIENCE AND TECHNOLOGY (TW)

( * ) Notice: Subject to any disclaimer, the term of this patent is extended or adjusted under 35 U.S.C. 154(b) by 0 days.

(21) Appl. No.: 15/205,083

(22) Filed: Jul. 8, 2016

(65) Prior Publication Data
US 2017/0226052 A1    Aug. 10, 2017

(30) Foreign Application Priority Data
Feb. 5, 2016 (TW) .............................. 105103908 A

(51) Int. Cl.
*C07C 245/08* (2006.01)

(52) U.S. Cl.
CPC .................................. *C07C 245/08* (2013.01)

(58) Field of Classification Search
CPC ..................................................... C07C 245/08
See application file for complete search history.

(56) References Cited

U.S. PATENT DOCUMENTS

| | | | |
|---|---|---|---|
| 7,144,960 B2 | 12/2006 | Jen et al. | |
| 7,268,188 B2 | 9/2007 | Jen et al. | |
| 7,390,857 B2 | 6/2008 | Cella et al. | |
| 7,425,643 B1 | 9/2008 | Jen et al. | |
| 8,173,045 B2 | 5/2012 | Jen et al. | |
| 8,394,499 B2 | 3/2013 | Jen et al. | |
| 8,409,713 B2 | 4/2013 | Jen et al. | |
| 8,648,332 B2 | 2/2014 | Jen et al. | |
| 2012/0252995 A1 | 10/2012 | Jen et al. | |

FOREIGN PATENT DOCUMENTS

| | | |
|---|---|---|
| TW | 085111870 | 12/1996 |
| TW | 200700461 | 6/2005 |
| TW | 200700462 | 6/2005 |
| TW | 201402681 A | 1/2014 |
| TW | 201412821 A | 4/2014 |

OTHER PUBLICATIONS

Yung-Chung Chen et al: Orderly Arranged NLO Materials Based on Chromophore-Containing Dendrons on Exfoliated Layered Templates; Applied Materials and Interfaces, vol. 1• No. 10• 2371-2381• 2009.

'Yung Chung Chen et al: Optical Non-Linearity from Montmorillonite Intercalated with a Chromophore-Containing Dendritic Structure: A Self-Assembly Approach, Macromol. Rapid Commun. 2008, 29, 587-592.

*Primary Examiner* — Shawquia Jackson
(74) *Attorney, Agent, or Firm* — Schmeiser, Olsen & Watts, LLP

(57) ABSTRACT

Epoxy/MMT composite material and a crosslinking method for epoxy/MMT composite material with second order nonlinear optical properties are introduced. Chromophore-containing intercalating agents are applied to modify montmorillonites (MMTs) to form organoclays by an ion-exchange process, wherein the chrmophores are neatly packed on exfoliated epoxy/organoclay nanocomposites. As a result, optical nonlinearity, i.e. the Pockels effect is observed for the nanocomposites without resorting to the poling process due to self-assembly process. Furthermore, a series of epoxy/MMT nanocomposites comprising thermally reversible furan-norbornene Diels-Alder adducts are prepared to establish a crosslinking feature. Self-alignment behavior, electro-optical (EO) coefficient and temporal stability of the epoxy/MMT nanocomposites are improved by the Diels-Alders crosslinking.

7 Claims, 7 Drawing Sheets

EPOXY RESIN OLIGOMER WITH SECOND ORDER NONLINEAR OPTICAL PROPERTIES, CHROMOPHORES, AND METHOD OF MANUFACTURING THE OLIGOMER-CONTAINING CROSSLINK LAYERED EPOXY/MMT COMPOSITE MATERIAL WITH SECOND ORDER NONLINEAR OPTICAL PROPERTIES

CROSS-REFERENCE TO RELATED APPLICATION

This non-provisional application claims priority under 35 U.S.C. § 119(a) on Patent Application No(s). 105103908 filed in Taiwan, R.O.C. on Feb. 5, 2016, the entire contents of which are hereby incorporated by reference.

FIELD OF THE INVENTION

The present invention relates to an epoxy resin oligomer with second order nonlinear optical properties, chromophores, a method of manufacturing the oligomer-containing crosslink layered epoxy/MMT composite material with second order nonlinear optical properties.

BACKGROUND OF THE INVENTION

Nonlinear optics describes the behavior of light in nonlinear media, that is, media in which the dielectric polarization responds nonlinearly to the electric field of the light, and the light can be exemplified by high-power laser. Weakly bonded valence electrons are polarized by the electric field, whereas the extent of polarization depends on the polarization of the molecules of the media and leads to a change in the distribution of the electric field of the ions of the media. Given the change in the distribution of the electric field of the ions of the media, dipole moment no longer linearly correlates with a light wave field, thereby resulting in a change in the phase, frequency and amplitude of light. The magnitude of the change is a function of incidence strength. Important components, such as those for use in processing, say regulating, turning on, turning off and storing, light-related information, are manufactured from materials with different nonlinear optical effects. The commonest conventional optoelectronic phase modulation device is designed according to the electro-optic (EO) effect of a second-order nonlinear optical material. Light controlling devices operating by the nonlinear optical effect include light modulation components and light switches. EO effect-based materials are capable of second harmonic generation (SHG) effectuated in a second order nonlinear manner and thereby exhibit first order electro-optic effect characterized by first-power proportional variations of the refractive index in accordance with the electric field. To meet the application requirement of nonlinear optical materials, an optical material must not only compulsorily exhibit a satisfactory nonlinear optical effect in a fixed direction and thereafter become fixed in place but also exhibit satisfactory high temperature stability.

Both Taiwan patent 200700461 and Taiwan patent 200700462 disclose novel chromophores derived from benzobisthiazole and polyimide which exhibits satisfactory thermal stability and disclose combining the two to achieve thermal stability and second order nonlinear optical characteristics. Although poly(benzobisthiazole) (PBT) exhibits satisfactory second order nonlinear optical characteristics, it cannot be completely dissolved in conventional organic solvents, thereby being limited in its application. To effectively enhance its solubility and maintain its good nonlinear optical characteristics, polyimide, which exhibits satisfactory solubility and processing properties, functions as a main chain. A chromophore derived from benzobisthiazole functions as a side chain which is grafted to the main chain of polyimide, so as to produce a polyimide which features thermal stability and second order nonlinear optical characteristics. Taiwan patent 085111870 provides a novel method of preparing a polymer film with second order nonlinear optical properties. The method is characterized in that molecules which have the nonlinear optical effect are doped by co-evaporation in the course of monomer vapor deposition and polymerization while undergoing polarization. One of the advantages of Taiwan patent 085111870 is that the film is manufactured in an extremely low polarization field and does not require any complicated polymerization process, thereby making it easy to manufacture numerous pieces of tailorable film of various types.

Taiwan patents 102127807 and 102112513 provide: a prepolymer for use in forming a nonlinear optical material which exhibits satisfactory nonlinear optical properties, thermal tolerance, insulation, compression tolerance, and transparency; a hardening material comprising the prepolymer; a composition comprising the hardening material and a solvent and adapted for use in coating; a nonlinear optical material formed by hardening the hardening material; and an optical waveguide using the nonlinear optical material and a light control device for use with the optical waveguide.

Directive hysteresis of an organic compound leads to a reduction in the nonlinear optical effect of the organic compound. This drawback is overcome by allowing an ion exchange reaction to take place between the organic compound and an organic intercalating agent, allowing admission and departure of monomers, and increasing an interlayer distance from 10 Å to 20~30 Å. In an intercalation state, layers are neatly arranged, distributed and spaced apart by a fixed distance, with organic molecules sandwiched between layers to go against action forces exerted upon and between layers and prevent re-stacking. In an exfoliation state, layers are spaced apart by irregular distances and are irregularly aligned. The organic intercalating agent increases the distance between the layers and increases the affinity between an inorganic layer and an organic polymer; afterward, an organic/inorganic polymer nano-composite material is produced by polymerization, fluxing processing or a redistribution mechanism.

Related research papers, namely Macromol. Rapid Commun., 2008, 29,587-592., Polym. Adv. Technol., 2009, 20, 493-500, ACS Applied Materials & Interfaces, 2009, 1, 2371-2381, Polym. Chem., 2013, 4, 2747-2759, disclose: producing an organic-modified clay from a dendritic polymer ended with chromophores, allowing intercalation to occur to its unique functional group and montmorillonite (MMT), and blending them with polyimide to form a nano-composite material, wherein the dendritic structure binds the chromophores and intercalates with an ionic group of the MMT so as to disarrange them by exfoliation. The mixed material not only exhibits an optoelectronic effect characterized by central asymmetry achieved readily by self-assembly without undergoing polarization but also exhibits satisfactory thermal stability.

Jen and others put forth patents, such as US20120252995 A1, U.S. Pat. No. 8,173,045 B2, U.S. Pat. No. 7,425,643 B1, U.S. Pat. No. 7,390,857 B2, U.S. Pat. No. 8,409,713 B2, U.S. Pat. No. 8,648,332 B2 and U.S. Pat. No. 8,394,499 B2, to disclose structures which undergo crosslinking by Diels-Alder reactions to effectuate second order central asymmetry and chemical structural combinations for use in Diels-Alder reversible reactions, as described in U.S. Pat. No. 7,268,188 B2 and U.S. Pat. No. 7,144,960 B2, wherein the stability of the second order nonlinear optical material is enhanced as a result of crosslinking.

SUMMARY OF THE INVENTION

The present invention relates to an epoxy resin oligomer with second order nonlinear optical properties, chromophores, and a method of manufacturing the oligomer-containing crosslink layered epoxy/MMT composite material with second order nonlinear optical properties, characterized in that: the epoxy resin oligomer composite material with second order nonlinear optical properties is acidified so that not only is a clay fully exfoliated and applicable to exfoliation of two-dimensional layered materials, including cation hydrotalcite, anionic silicate clay and layered graphite with organic groups, but the chromophores also becomes central asymmetry. After undergoing crosslinking, the composite material exhibits fixed central asymmetry and enhanced thermal stability.

It is an objective of the present invention to provide a method of fixing central asymmetric arrangement of a second order nonlinear optical material by organic exfoliation. Dicyclopentadiene (DCPD) is a precursor of adamantane, exhibits satisfactory copolymerization, enhances electrical and mechanical properties of materials, and enhances weatherability and thermal tolerance of materials, and therefore is widely applied in specific chemicals. According to the present invention, side chain groups with double bonds are produced by a reaction of norbornene (a derivative of cyclopentadiene) and the alcohols of epoxy resin, and then the side chain groups with double bonds and an epoxy resin with a furan side chain undergo Diels-Alder crosslinking, so as to fix the central asymmetry of a crosslink layered epoxy/MMT composite material with second order nonlinear optical properties and enhance the thermal stability of the material.

Another objective of the present invention is to provide an epoxy resin oligomer with second order nonlinear optical properties, chromophores, and a method of manufacturing the oligomer-containing crosslink layered epoxy/MMT composite material with second order nonlinear optical properties, and synthesize a polymer composite material with second order nonlinear optical activity from diamine chromophores and diglycidyl ether of bisphenol A (DGEBA). The diamine chromophore is either bis(4-aminophenyl(4-(4-nitrophenyl)-diazenyl)-phenyl) amine, DAC compound, or 2,4-diamino-4'-(4-nitrophenyl-diazenyl)-azobenzene, DNDA compound, and is expressed by the structural formula as follows:

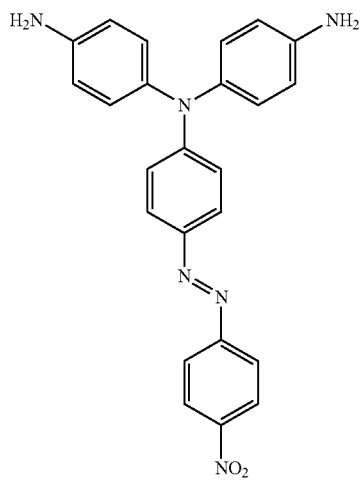

DAC

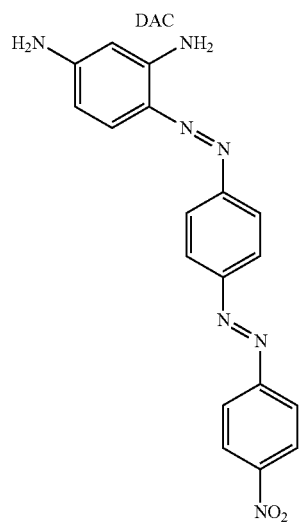

DNDA

The epoxy resin is diglycidyl ether of bisphenol A (DGEBA) and is expressed by the structural formula as follows:

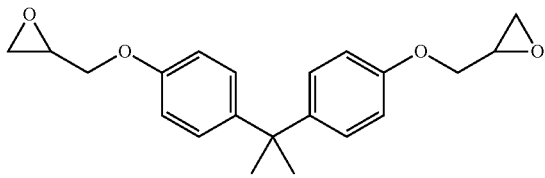 [SMILES: CC(C)(c1ccc(OCC2CO2)cc1)c1ccc(OCC2CO2)cc1]

The synthesis of the polymer composite material with second order nonlinear optical activity from the diamine chromophores and diglycidyl ether of bisphenol A (DGEBA) must take place in the presence of nitrogen gas, at 100~150° C. and for 24~48 hours to preclude any crosslinking reaction. The linear second order nonlinear epoxy resin molecular weight (Mn) falls within the range of 5000~14000 g/mol, whereas polydispersity ranges from 2.1 to 3.2. Upon completion of polymerization, ultraviolet-visible spectroscopy (UV-Vis) is performed to confirm that second order nonlinear chromophore optical absorption wavelength has not vanished and the reaction has not damaged chromophores.

A method of exfoliating MMT with an epoxy resin composite material requires a two-dimensional layered material, using MMT as a raw material, allowing acidified second order nonlinear optical material oligomer secondary amine to carry cations and undergo ion exchange with sodium ions carried between MMT layers, thereby exfoliating MMT above 1CEC (cation exchange capacity, 1.20 mequiv/g for Na+MMT). 50 mL of deionized water is added to each gram of MMT to effectuate swelling at 80° C. for 24 hours until it is uniformly dispersed. In this regard, MMT, mica, kaolin, vermiculite, hydrotalcite (layered double hydroxides, LDH) and exfoliatable two-dimensional layered materials can be exfoliated. In the aforesaid step, the cosolvent is an aprotic polar hydrophilic solvent, such as N,N-Dimethylacetamide (DMAc), dimethylfomamide (DMF), (dimethylsulfoxide (DMSO), and 1-methyl-2-pyrrolidone (NMP). The ionic inorganic acid is sulfuric acid, nitric acid, hydrochloric acid, phosphoric acid or any acid with an equivalent effect. Then, secondary amine which equals the acid in equivalent weight is introduced to effectuate acidification so that the second order nonlinear epoxy resin composite material has a pH of 3.5~4.3. Applicable epoxy resin composite materials must have a CEC of 1~5. Upon completion of exfoliation, the epoxy resin composite material of MMT undergoes self-assembly to become a second order nonlinear optical material with a second order nonlinear optical properties $r_{33}$ coefficient of 2.4~4.7 pm/V.

A method of crosslinking layered epoxy/MMT composite material with second order nonlinear optical properties involves grafting norbornene and furan side chain to alcohols of epoxy resin composite material of second order nonlinear optical properties MMT, respectively, and thereby carrying out Diels-Alder reaction thermal crosslinking (shown in FIG. 8) before fixing the central asymmetry of the second order nonlinear optical material.

DETAILED DESCRIPTION OF THE PREFERRED EMBODIMENTS

Figure 1:
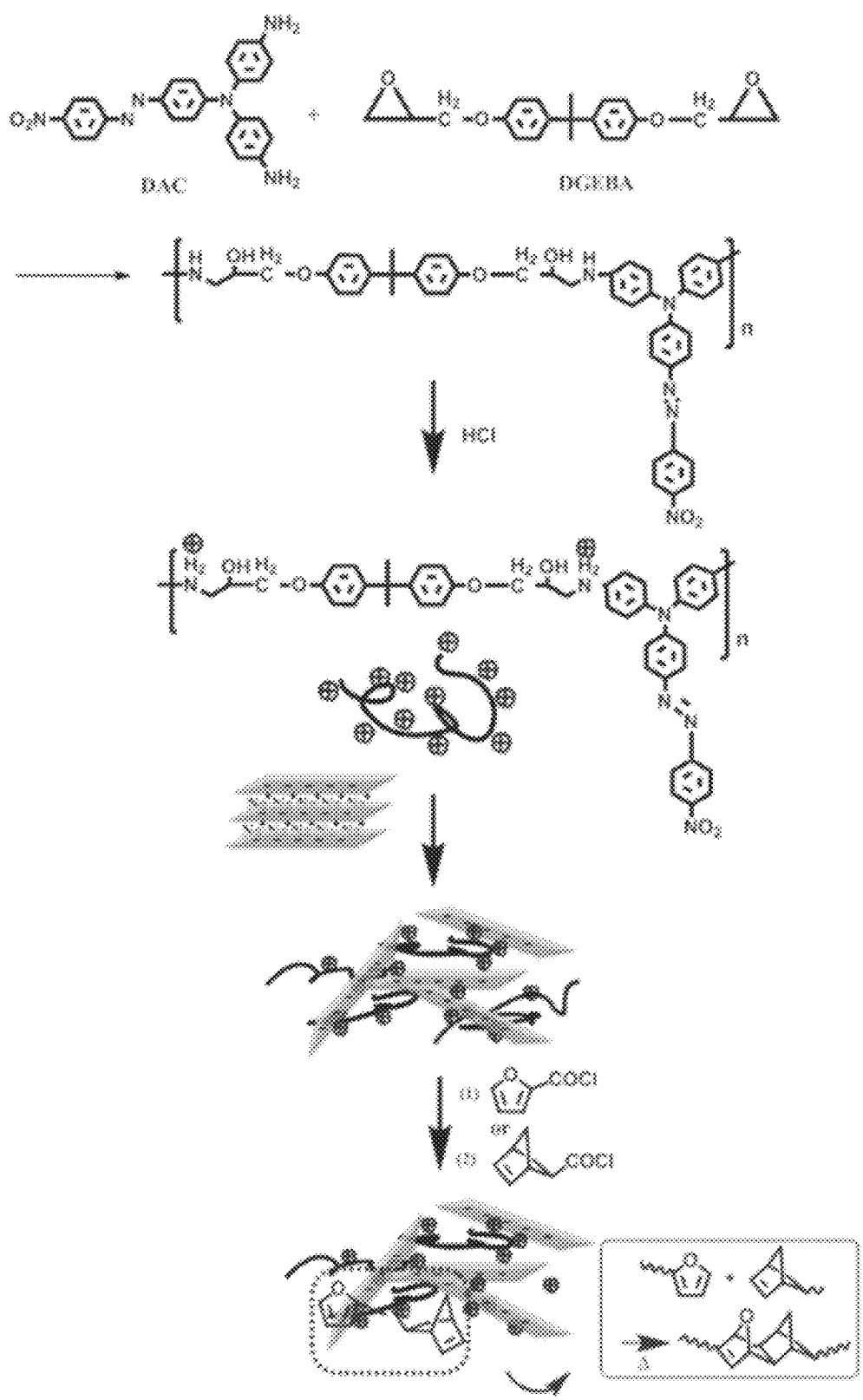
FIG. 1 is a schematic view of synthesis of second order nonlinear epoxy resin oligomer according to the present invention.

The manufacturing process of the present invention is illustrated with preferred embodiments. Manufacturing criteria and results of the present invention are illustrated with comparisons.

Embodiment 1

Step (a): synthesis of epoxy resin oligomer with second order nonlinear optical properties dissolving 1.22 g (8 mmole) of p-nitrosonitrobenzene and 4.07 g (14 mmole) of 4,4',4"-triamino-phenylamine in an appropriate amount of acetic acid, instilling p-nitrosonitrobenzene solution slowly into 4,4',4"-triaminophenylamine solution, blending them so that they react for 12 hours, neutralizing it with acetic acid sodium saturated solution to pH 6 such that purple solid precipitate is produced, performing solid-liquid separation by suction filtration, and rinsing the filter disk with a large amount of deionized water in several instances to obtain a purple solid mixture, wherein the collected solid mixture is purified by column chromatography to extract a product therefrom, wherein an eluent of n-hexane:ethyl acetate is of a ratio 1:3, so as to produce DAC, which is a bright green solid, and the aforesaid chemical reaction is expressed by the structural formulas as follows:

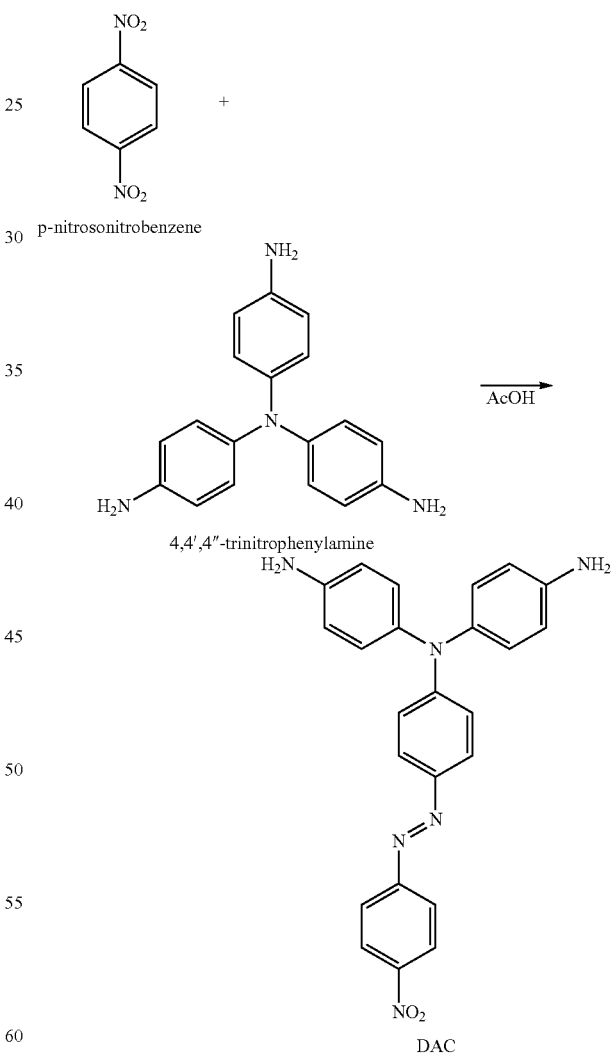

mixing 2 g (6 mmol) of DGEBA and 2 g (6 mmol) of DAC uniformly to allow polymerization to take place at 150° C. for 40 hours, and then instilling the mixture, drop by drop, into 50 mL of $CH_3OH$ and blending it to produce DGEBA-DAC oligomer (DACP). The aforesaid chemical reaction is monitored with FTIR. The completion of the aforesaid chemical reaction is confirmed by the disappearance of the absorption peak of the characteristics of the epoxy group with a wave number of 913 cm$^{-1}$. The aforesaid chemical reaction is expressed by the structural formulas as follows:

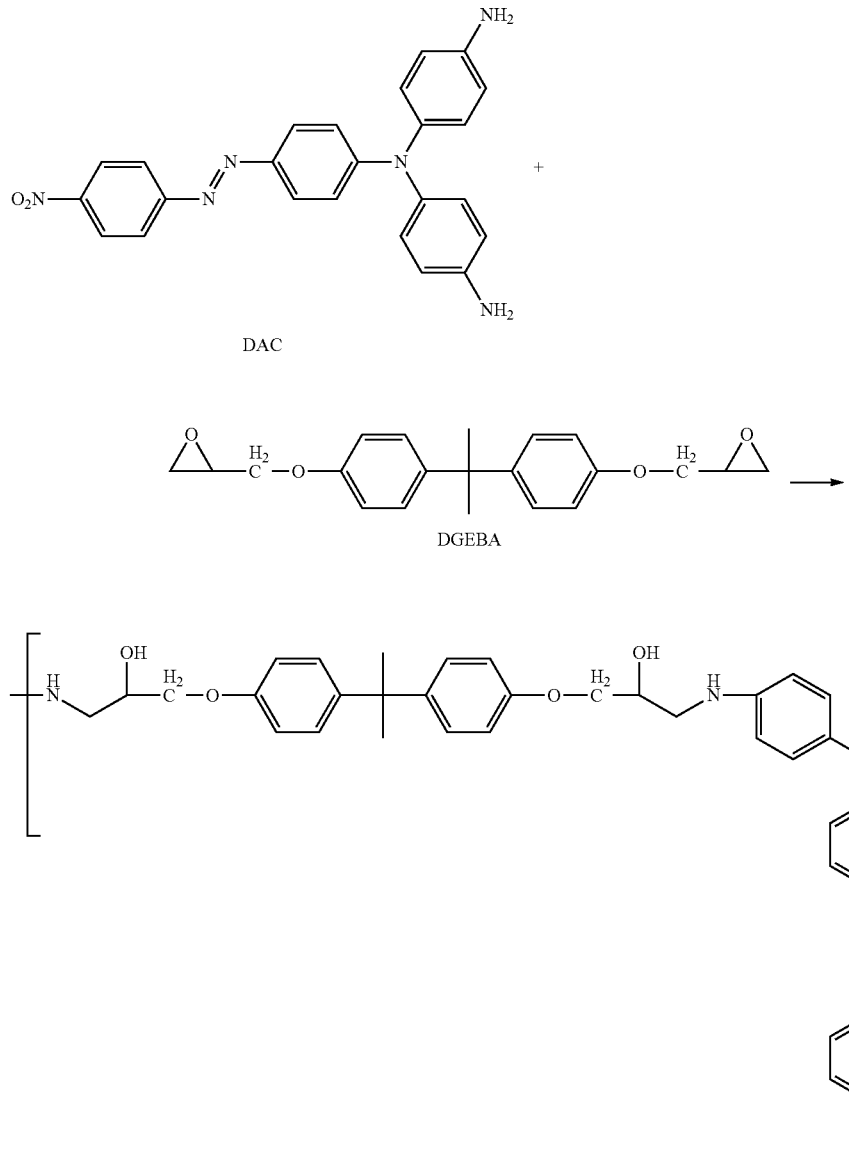

where n is 3~10.

Step (b): modifying montmorillonite (MMT) with DGEBA-DAC oligomer allowing DGEBA (1.6 g, 4.7 mmol) and DAC (2 g, 4.7 mmol) to undergo polymerization at 150° C., wherein the polymerization temperature is determined by DSC. Polymer crosslinking begins to take place as soon as the temperature increases to above 150° C., thereby precluding dissolution. Hence, when the temperature is below 150° C., DGEBA and primary amine react for 24 hours. The aforesaid chemical reaction is monitored with FTIR. The completion of the aforesaid chemical reaction is confirmed by the disappearance of the absorption peak of the characteristics of the epoxy group with a wave number of 913 cm$^{-1}$. The resultant oligomer (abbreviated as DCAP, Mn=5000~14000 g/mol) can be directly dissolved in a solvent (DMAc) to undergo ion exchange with MMT (1.20 mequiv/g for Na$^+$ MMT) by amine titration and acidification of oligomers. The second order nonlinear optical characteristics of the exfoliated oligomer MMT composite material are measurable. For details, see Macromol. Rapid Commun., 2008, 29,587-592.; Polym. Adv. Technol., 2009, 20, 493-500.; ACS Applied Materials & Interfaces, 2009, 1, 2371-2381, Polym. Chem., 2013, 4, 2747-2759.

Step (c): crosslinking and solidifying DGEBA-DAC

The nano-composite material (DACPMMT for short), which is produced by modifying MMT with oligomers and exhibits second order central asymmetry, is uniformly dispersed in the solvent DMAc. Then, 0.25 g of 2-Furoyl chloride is introduced into 1.96 g of DACPMMT to react at room temperature for 24 hours so that the product DACPMMT-F is obtained by extraction. The aforesaid steps are repeated. Afterward, 0.31 g of 5-Norbornene-2-carbonyl chloride is added to 1.96 g of DACPMMT to react at room temperature for 24 hours so that the product DACPMMT-N is obtained by extraction. Finally, DACPMMT-F and DACPMMT-N which are equal in equivalent weight react at an appropriate temperature determined by DSC. Eventually, the reaction temperature of the Diels-Alder reaction is set to 237° C. The Diels-Alder reaction enables the modified DACPMMT to form a reticular crosslinking structure characterized by crosslinking solidification and second order central asymmetry.

Afterward, solid-liquid separation is performed by filter funnel-based filtration, and then the filter disk is rinsed with a large amount of distilled water until the filtrate attain neutrality (pH 6~7), wherein an eluent of n-hexane:ethyl acetate is of a ratio 1:3, so as to produce chromophore DNDA. The chemical reaction is expressed by the structural formulas as follows:

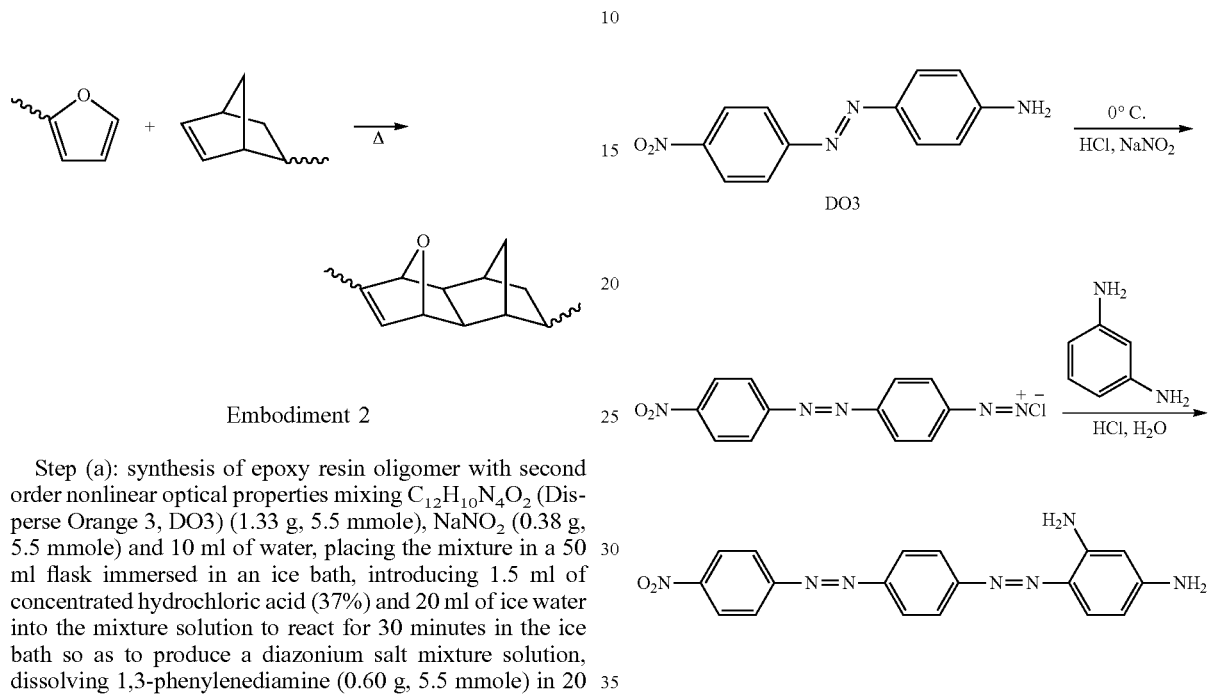

Embodiment 2

Step (a): synthesis of epoxy resin oligomer with second order nonlinear optical properties mixing $C_{12}H_{10}N_4O_2$ (Disperse Orange 3, DO3) (1.33 g, 5.5 mmole), $NaNO_2$ (0.38 g, 5.5 mmole) and 10 ml of water, placing the mixture in a 50 ml flask immersed in an ice bath, introducing 1.5 ml of concentrated hydrochloric acid (37%) and 20 ml of ice water into the mixture solution to react for 30 minutes in the ice bath so as to produce a diazonium salt mixture solution, dissolving 1,3-phenylenediamine (0.60 g, 5.5 mmole) in 20 ml of distilled water and 3 ml of concentrated hydrochloric acid (37%) and placing the solution in another 50 ml flask, adding the diazonium salt solution into the flask slowly and blending the solution therein for 1 hour approximately to finalize the chemical reaction. A sodium hydroxide aqueous solution is prepared and used to neutralize the aforesaid solution such that a dark brown solid precipitate is formed.

wherein $C_{12}H_{10}N_4O_2$ (Disperse Orange 3, DO3) has a molecular weight of 242.23 g/mol. mixing 2 g (6 mmol) of DGEBA and 2 g (6 mmol) of DNDA uniformly, allowing the mixture to undergo polymerization at 150° C. for 40 hours, instilling 50 mL of $CH_3OH$ into the mixture, and blending the mixture to obtain DGEBA-DNDA oligomer (DNDAP):

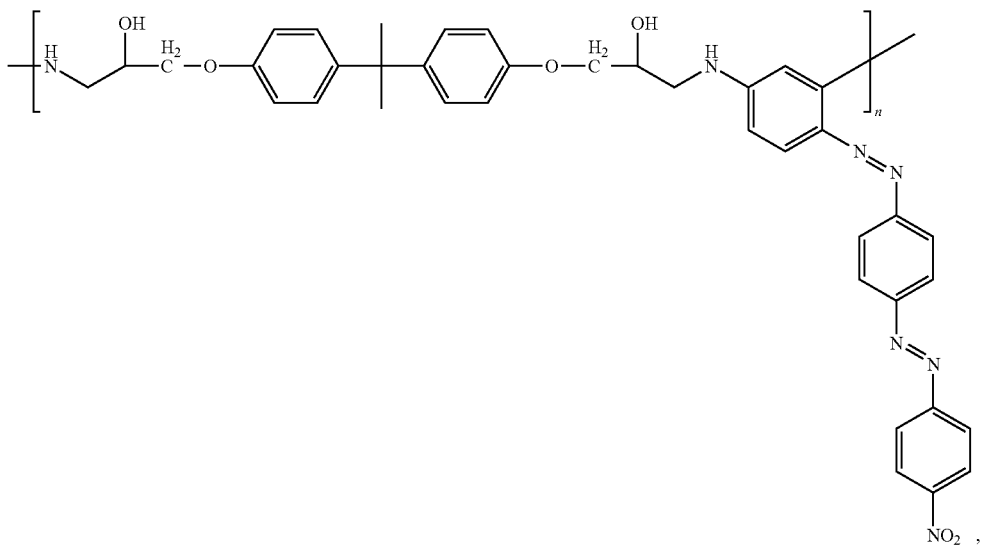

where n is 3~10. The aforesaid chemical reaction is monitored with FTIR. The completion of the aforesaid chemical reaction is confirmed by the disappearance of the absorption peak of the characteristics of the epoxy group with a wave number of 913 cm$^{-1}$.

Step (b): modifying MMT with DGEBA-DNDA oligomer DGEBA (1.6 g, 4.7 mmol) and DNDA (2 g, 4.7 mmol) undergo polymerization at 150° C., wherein the polymerization temperature is determined by DSC. Polymer crosslinking begins to take place as soon as the temperature increases to above 150° C., thereby precluding dissolution. Hence, when the temperature is below 150° C., DGEBA and primary amine react for 24 hours. The aforesaid chemical reaction is monitored with FTIR. The completion of the aforesaid chemical reaction is confirmed by the disappearance of the absorption peak of the characteristics of the epoxy group with a wave number of 913 cm$^{-1}$. The resultant oligomer (abbreviated as DNDAP, Mn=5000~14000 g/mol) can be directly dissolved in a solvent (DMAc) to undergo ion exchange with MMT (1.20 mequiv/g for Na$^+$ MMT) by amine titration and acidification of oligomers. The second order nonlinear optical characteristics of the exfoliated oligomer MMT composite material are measurable. For details, see Macromol. Rapid Commun., 2008, 29,587-592.; Polym. Adv. Technol., 2009, 20, 493-500.; ACS Applied Materials & Interfaces, 2009, 1, 2371-2381, Polym. Chem., 2013, 4, 2747-2759.

Step (c): crosslinking solidifying DGEBA-DNDA The nano-composite material (DNDAPMMT for short), which is produced by modifying MMT with oligomers and exhibits second order central asymmetry, is uniformly dispersed in the solvent DMAc. Then, 0.25 g of 2-Furoyl chloride is introduced into 1.96 g of DNDAPMMT to react at room temperature for 24 hours so that the product DNDAPMMT-F is obtained by extraction. The aforesaid steps repeat, and then 0.31 g of 5-Norbornene-2-carbonyl chloride is added to 1.96 g of DNDAPMMTMMT to react at room temperature for 24 hours so that the product DNDAPMMT-N is obtained by extraction. Finally, DNDAPMMT-F and DNDAPMMT-N which are equal in equivalent weight react at an appropriate temperature determined by DSC. Eventually, the reaction temperature of the Diels-Alder reaction is set to 237° C. The Diels-Alder reaction enables the modified DNDAPMMT to form a reticular crosslinking structure characterized by crosslinking solidification and second order central asymmetry.

Figure 2:
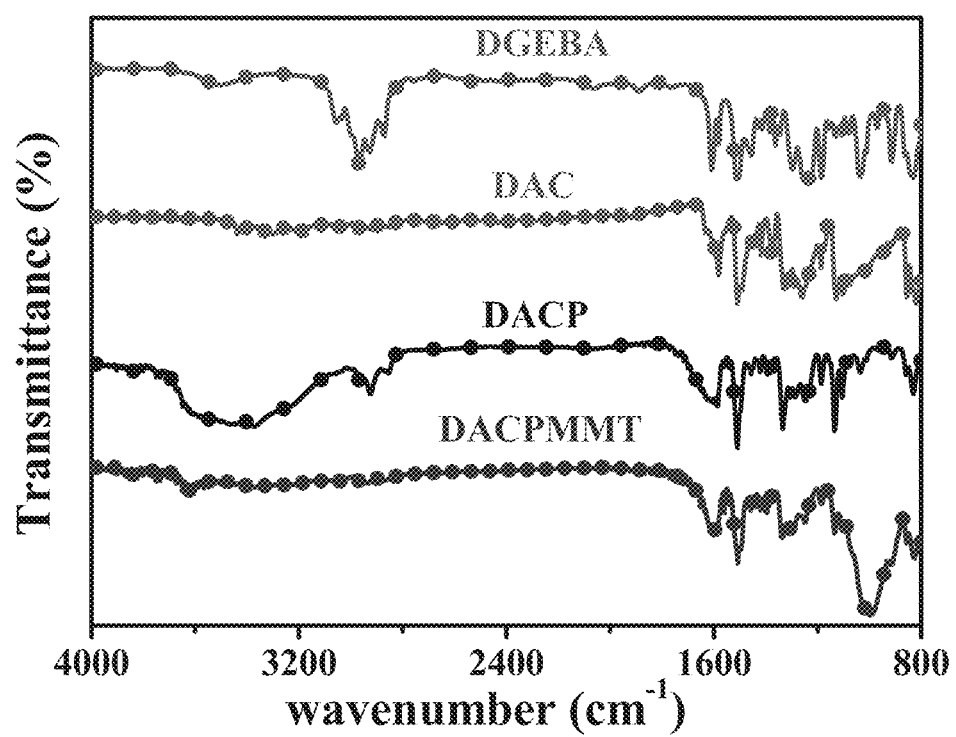
FIG. 2 is a graph of IR variations of DACP polymerization group according to the present invention.
Figure 3:
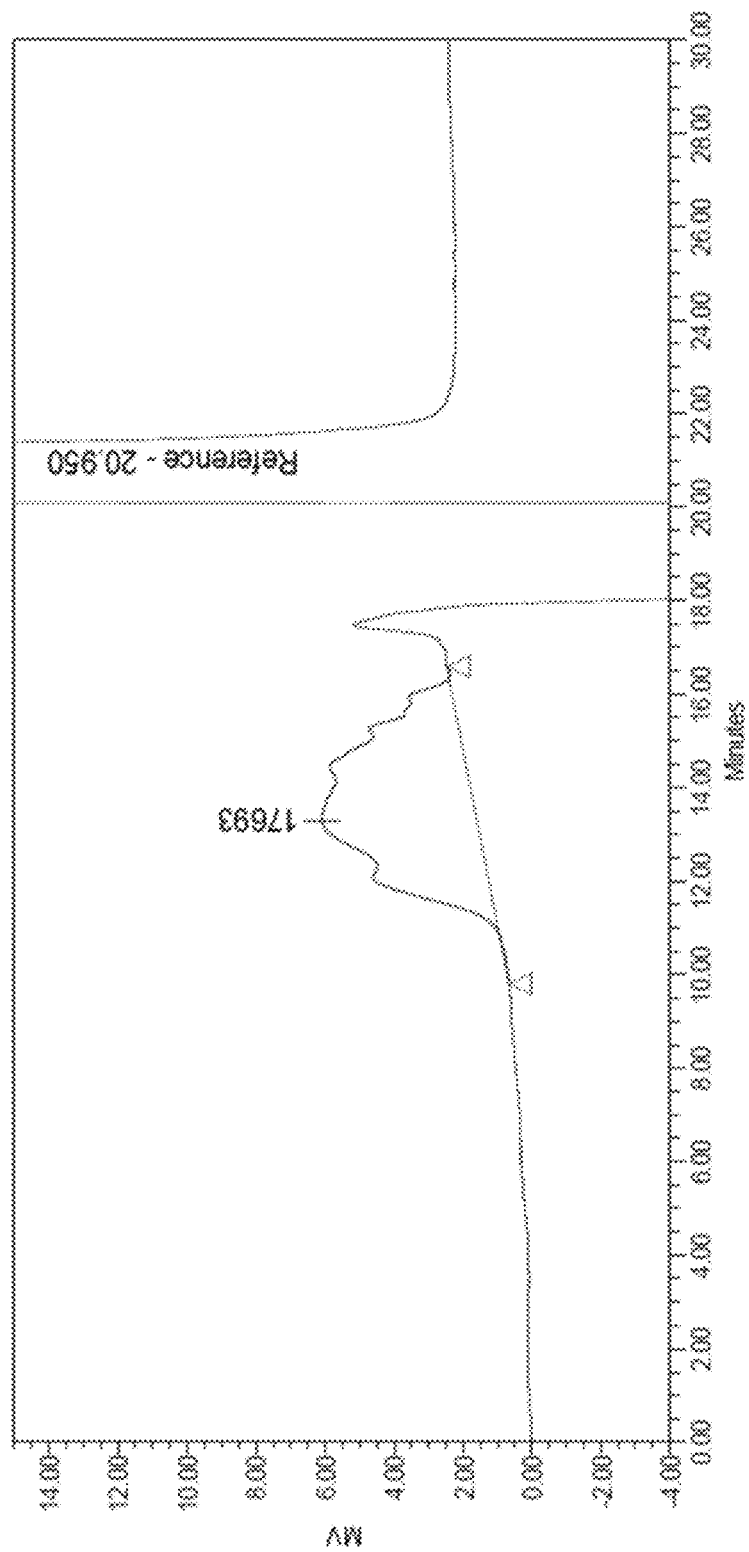
FIG. 3 is a graph of molecular weight of second order nonlinear optical oligomer according to the present invention.

Referring to FIG. 1, DGEBA and DAC undergo polymerization at 150° C., wherein the polymerization temperature is determined by DSC. Polymer crosslinking begins to take place as soon as the temperature increases to above 150° C., thereby precluding dissolution. Hence, when the temperature is below 150° C., DGEBA and primary amine react for 24 hours. The aforesaid chemical reaction is monitored with FTIR as shown in FIG. 2. The completion of the aforesaid chemical reaction is confirmed by the disappearance of the absorption peak of the characteristics of the epoxy group with a wave number of 913 cm$^{-1}$. The resultant oligomer (abbreviated as DCAP) whose average molecular weight is around 8000 as indicated by GPC analysis shown in FIG. 3. DACP is soluble in solvents, such as THF, DMAc, to undergo ion exchange with MMT by amine titration and acidification of oligomers so that MMT attains exfoliation quickly and easily. The exfoliated oligomer MMT composite material undergo XRD, TEM, thermal analysis and optoelectronic property test and thereby the composite material is found to exhibit a second order nonlinear optical properties $r_{33}$ coefficient of 8.0.

Figure 4:
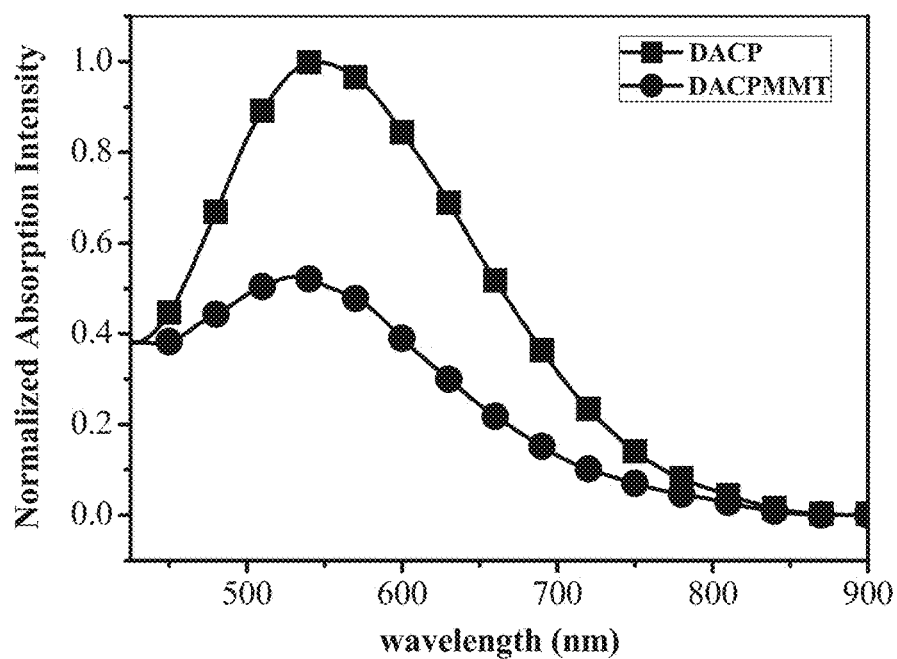
FIG. 4 is a UV-Vis spectrogram of second order nonlinear optical material oligomer according to the present invention.
Figure 5:
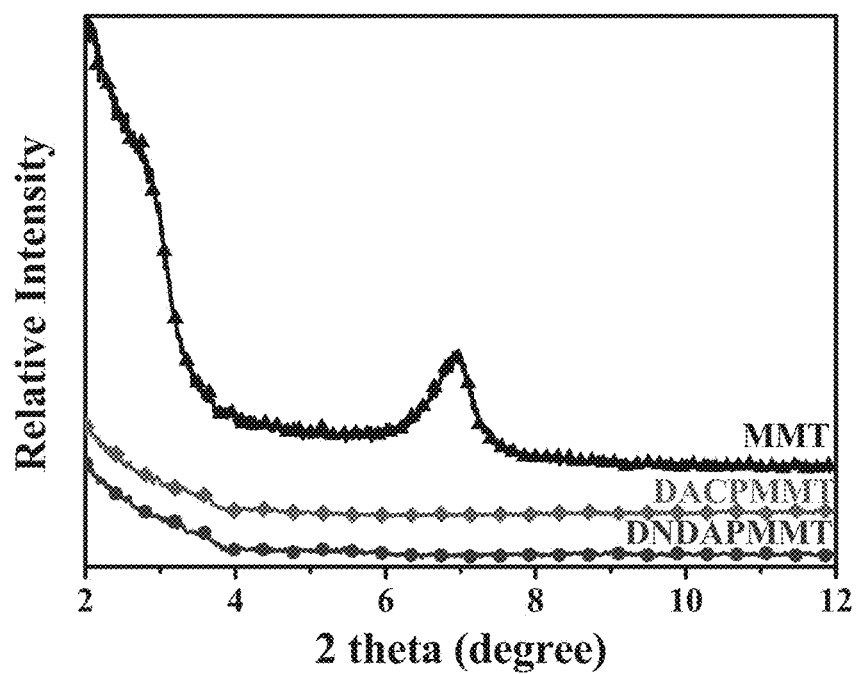
FIG. 5 is MMT exfoliation XRD spectrogram according to the present invention.

With positive charges being carried between the MMT layers, it is necessary to acidify polymers in order for cation exchange to occur, thereby necessitating the second order nonlinear optical oligomer intercalation step shown in FIG. 2 so that polymers which end up between the layers can further exfoliate MMT. The IR spectrogram shows the changes which occur to the epoxy group before and after polymerization, wherein the absorption of intercalated MMT leads to the disappearance of DACP IR characteristic peak. Referring to FIG. 4, the UV-Vis spectrogram shows that 547 cm$^{-1}$DAC characteristic absorption peak still features slight red displacement. Hence, the UV-Vis spectrogram of FIG. 4 and the MMT exfoliation XRD spectrogram of FIG. 5 together prove that crosslink layered epoxy/MMT composite material with second order nonlinear optical properties not only separates the layers of MMT but also retains the initial second order nonlinear optical chromophores, as substantiated by the measurement of the second order nonlinear optical characteristics shown in Table 1.

Figure 6:
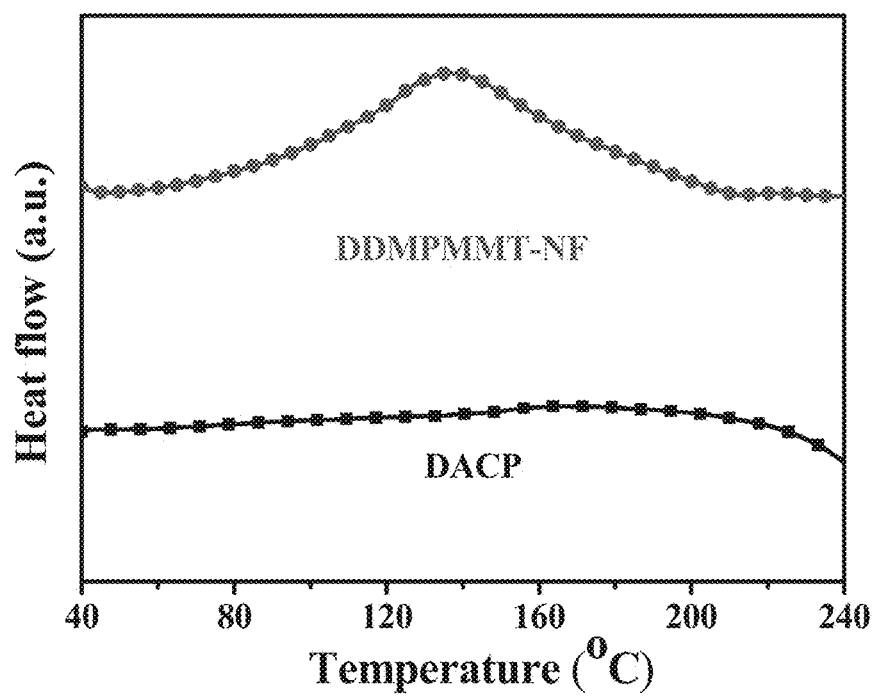
FIG. 6 is a graph of Diels-Alder crosslinking reaction temperature changes observed by DSC according to the present invention.
Figure 7:
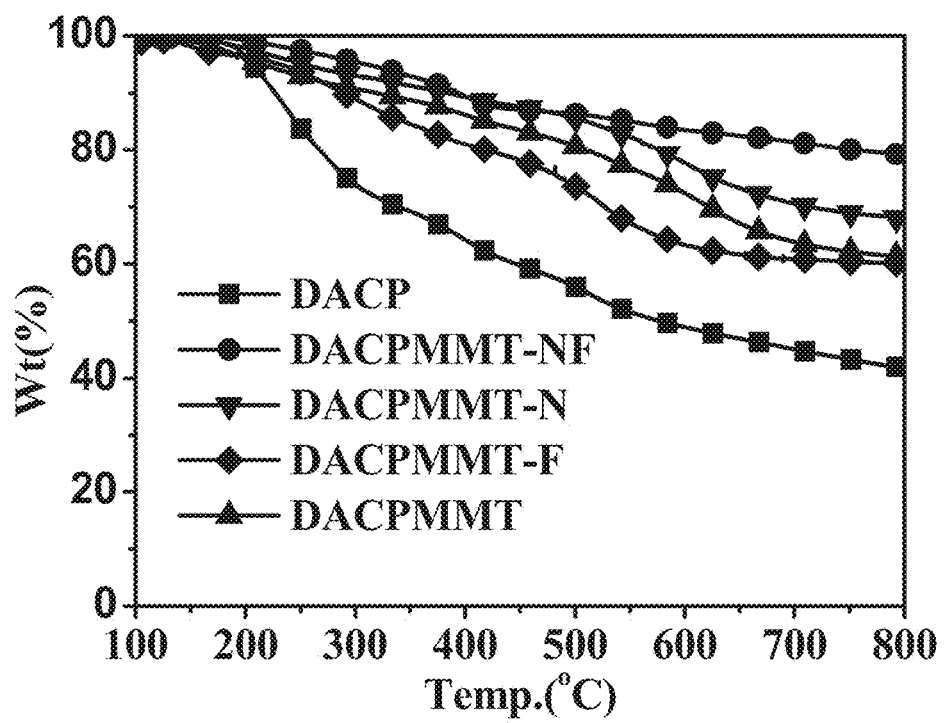
FIG. 7 is a graph of pyrolysis temperature changes observed by TGA before and after Diels-Alder crosslinking according to the present invention.
Figure 8:
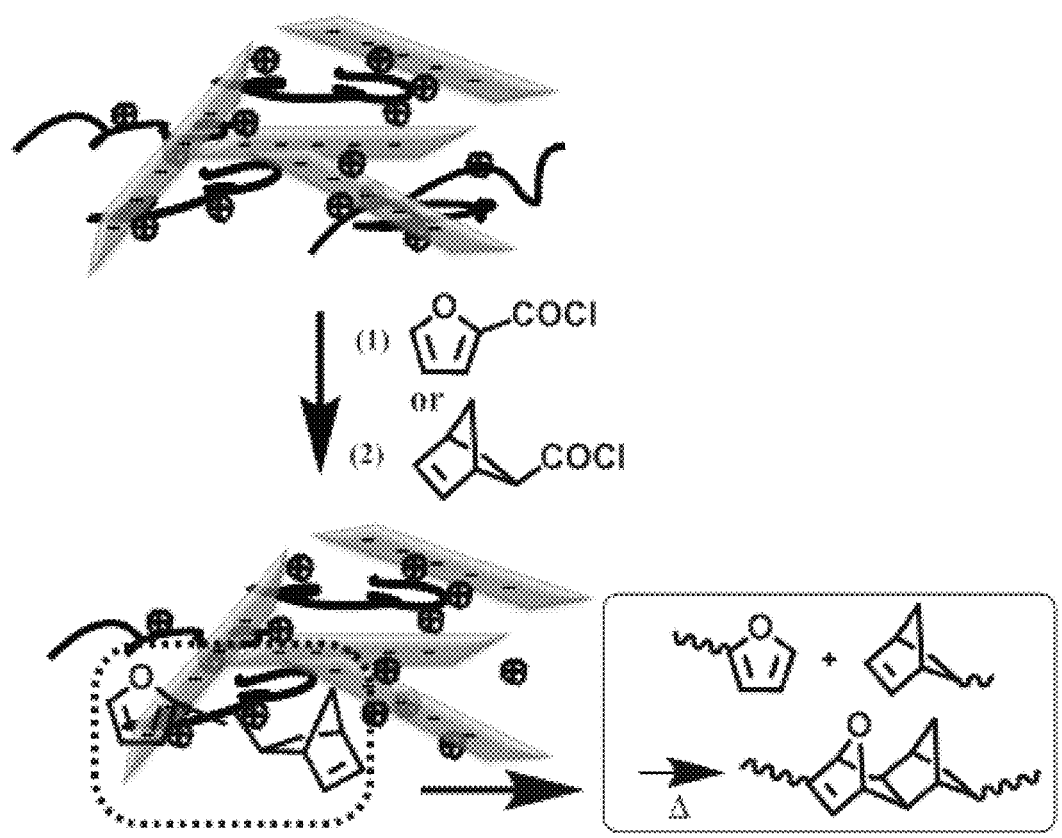
FIG. 8 is a schematic view of the Diels-Alder reaction thermal crosslinking according to the present invention.
Figure 9:
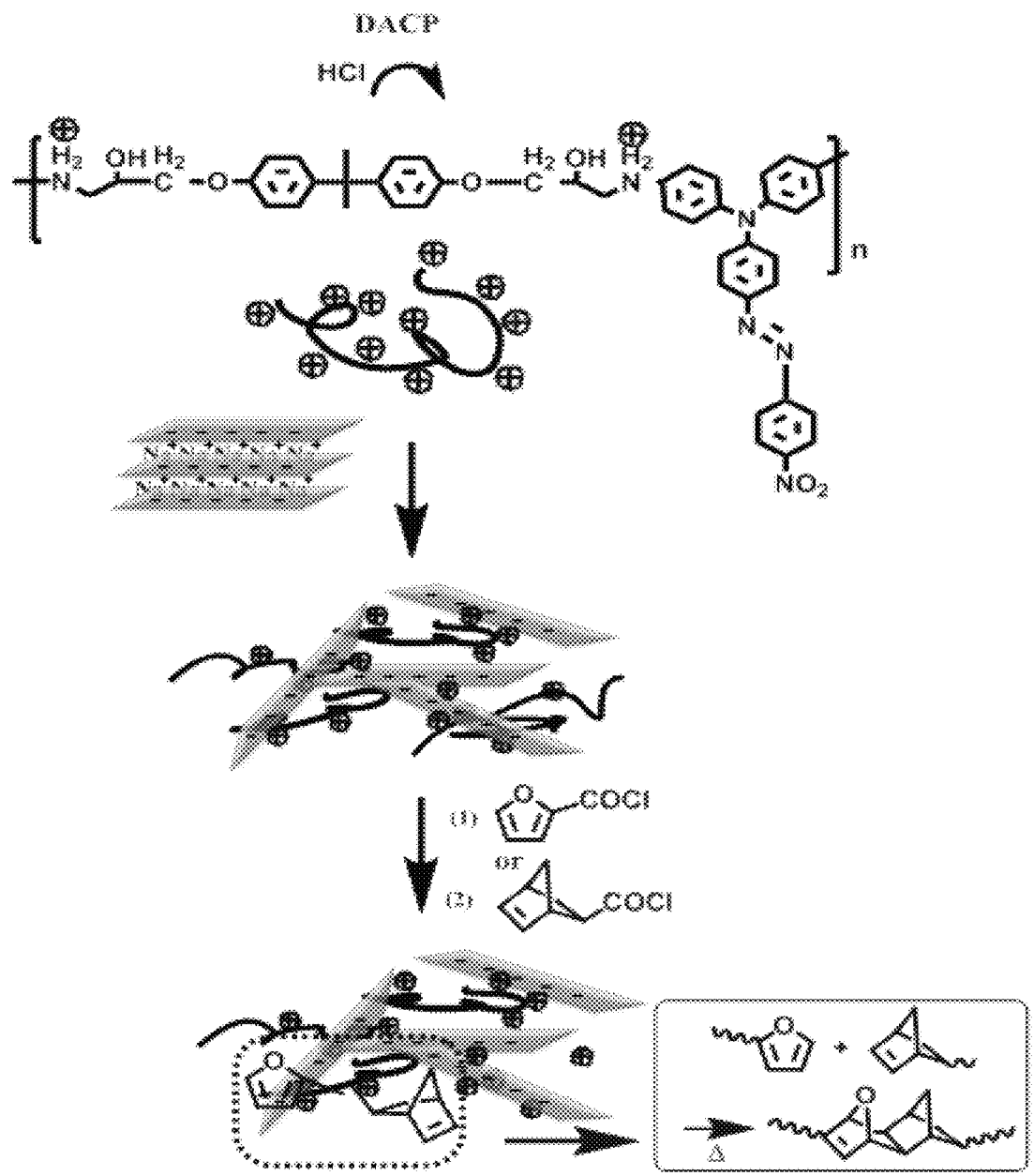
FIG. 9 is a schematic view of modifying MMT with DGEBA-DAC oligomer according to the present invention.

The exfoliated epoxy/MMT composite material with second order nonlinear optical properties is modified and grafted to the furan functioning as the diene and the norbornene functioning as the dienophile during the Diels-Alder reaction. The DSC of FIG. 6 shows a Diels-Alder reaction exothermic peak which is otherwise initially absent from DACP and thereby confirms the occurrence of the crosslinking reaction. Upon completion of crosslinking, the central asymmetry of the second order nonlinear optical material is fixed so that a second order nonlinear optical properties r33 coefficient of 2.1 of the optical material can be detected even at 120° C. FIG. 7 is a graph of pyrolysis temperature changes in DACP before crosslinking and DAC after crosslinking, showing that 5 wt % thermogravimetric loss temperature increases from 220° C. of DACPMMT to 310° C. of DACPMMT-NF so that an increase in the pyrolytic temperature improves the material operating range.

What is claimed is:

1. An epoxy resin oligomer with second order nonlinear optical properties, represented by one of structural formula as follows:

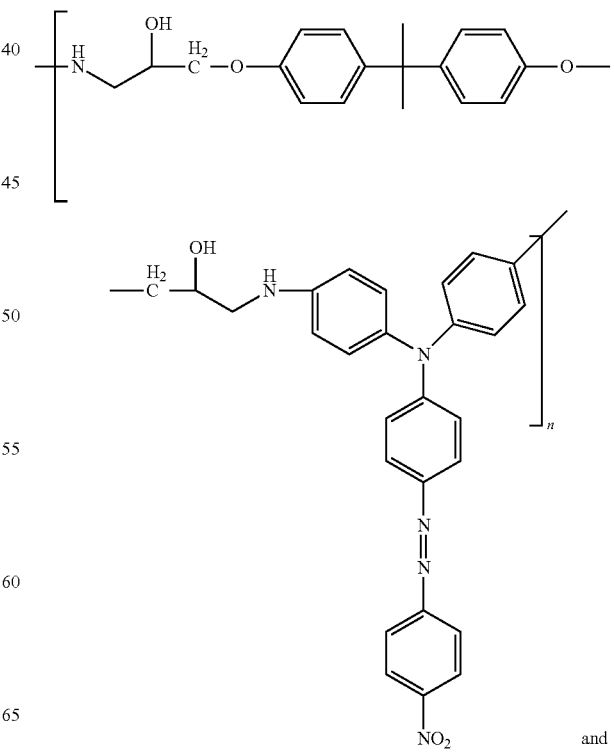

and

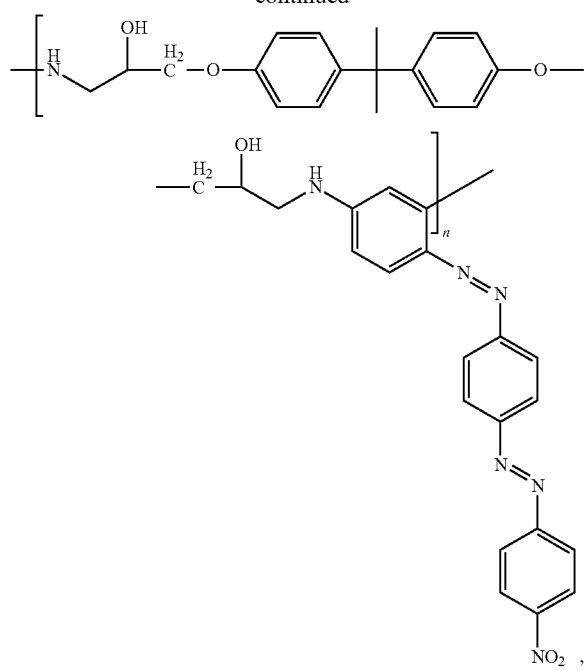

where n is 3~10.

2. A method of manufacturing a crosslink layered epoxy/MMT composite material with second order nonlinear optical properties according to claim 1, comprising the steps of:
   (a) dissolving p-nitrosonitrobenzene and 4,4',4"-triamino-phenylamine in acetic acid to form p-nitrosonitrobenzene solution and 4,4',4"-triamino-phenylamine solution, respectively;
   (b) instilling p-nitrosonitrobenzene solution into 4,4',4"-triamino-phenylamine solution, blending the solutions to allow a reaction to occur thereto, so as to obtain diamine chromophores bis(4-aminophenyl(4-(4-nitrophenyl)-diazenyl)phenyl)amine (DAC compound) as expressed by a structural formulas as follows:

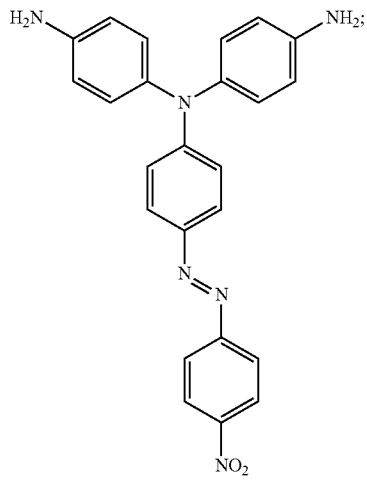 [SMILES: Nc1ccc(N(c2ccc(N)cc2)c2ccc(/N=N/c3ccc([N+](=O)[O-])cc3)cc2)cc1]

(c) mixing diglycidyl ether of bisphenol A (DGEBA) expressed by structural formula

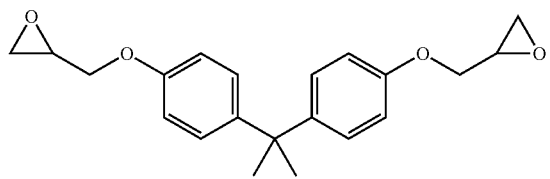 [SMILES: CC(C)(c1ccc(OCC2CO2)cc1)c1ccc(OCC2CO2)cc1]

and DAC uniformly to allow a polymerization reaction to take place in presence of nitrogen gas, at a constant temperature range and for a specific period of time to obtain DGEBA-DAC oligomer; and
   (d) allowing ion exchange to occur between DGEBA-DAC oligomer and montmorillonite (MMT) such that the crosslink layered epoxy/MMT composite material exhibits second order nonlinear optical properties.

3. The method of claim 2, wherein the constant temperature range is 100~150° C.

4. The method of claim 2, wherein the polymerization reaction lasts for 24~48 hours.

5. A method of manufacturing a crosslink layered epoxy/MMT composite material with second order nonlinear optical properties according to claim 1, comprising the steps of:
   (a) mixing DO3, NaNO$_2$ and water, followed by adding concentrated hydrochloric acid to the aqueous mixture;
   (b) adding ice water to the solution formed in step (a) to allow a reaction to occur in an ice bath, thereby forming a diazonium salt mixture solution;
   (c) adding the diazonium salt mixture solution formed in step (b) to 1,3-phenylenediamine solution, followed by blending them to allow a reaction to occur thereto;
   (d) mixing sodium hydroxide aqueous solution and the solution formed in step (c) to obtain diamine chromophores 2,4-diamino-4'-(4-nitrophenyl-diazenyl)-azobenzene (DNDA compound) as expressed by a structural formulas as follows:

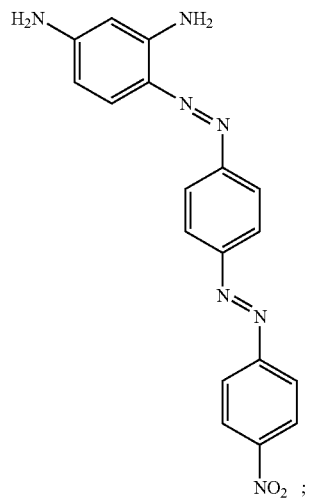 [SMILES: Nc1ccc(N=Nc2ccc(/N=N/c3ccc([N+](=O)[O-])cc3)cc2)c(N)c1]

(e) mixing diglycidyl ether of bisphenol A (DGEBA) expressed by structural formula

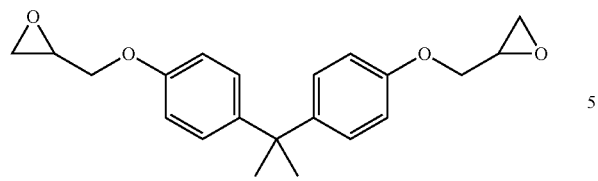

and DNDA uniformly to allow a polymerization reaction to take place in presence of nitrogen gas, at a constant temperature range and for a specific period of time to obtain DGEBA-DNDA oligomer; and (f) allowing ion exchange to occur between DGEBA-DNDA oligomer and montmorillonite (MMT) such that the crosslink layered epoxy/MMT composite material exhibits second order nonlinear optical properties.

6. The method of claim 5, wherein the constant temperature range is 100~150° C.

7. The method of claim 5, wherein the polymerization reaction lasts for 24~48 hours.

\* \* \* \* \*